United States Patent [19]

Grimmer

[11] Patent Number: 4,806,643
[45] Date of Patent: Feb. 21, 1989

[54] PREPARATION OF RIBOFLAVIN

[75] Inventor: Johannes Grimmer, Ludwigshafen, Fed. Rep. of Germany

[73] Assignee: BASF Aktiengesellschaft, Ludwigshafen, Fed. Rep. of Germany

[21] Appl. No.: 932,312

[22] Filed: Nov. 19, 1986

[30] Foreign Application Priority Data

Dec. 4, 1985 [DE] Fed. Rep. of Germany ....... 3542837

[51] Int. Cl.⁴ .......................................... C07D 475/14
[52] U.S. Cl. .................................................. 544/251
[58] Field of Search ........................................ 544/251

[56] References Cited

U.S. PATENT DOCUMENTS 4,567,261 1/1986 Ernst et al. ........................... 544/251
4,656,275 4/1987 Ernst et al. ........................... 544/251
4,673,742 6/1987 Grimmer et al. ................... 544/251

FOREIGN PATENT DOCUMENTS 0161548 10/1985 European Pat. Off. ............ 544/251
3302497 7/1984 Fed. Rep. of Germany ...... 544/251
3406319 8/1985 Fed. Rep. of Germany ...... 544/251

OTHER PUBLICATIONS

J.A.C.S., vol. 69, (1947), pp. 731, 1487–1491; "Thirteenth Report of the Committee on Atomic Weights of the International Union of Chemistry", Baxter et al. and "...New Synthesis of Riboflavin" by Tishler et al. (Berezovskii et al.).
J. Gen. Chem. USSR, (1961), vol. 31, pp. 3444–3448, "Investigations in the Alloxazine and Isoalloxazine Series v. Catalysts for the Reaction of Secondary Aromatic Orthoaminoazo Compounds with Trihydroxypyrimidines".
J.A.C.S., vol. 76, (1954), pp. 2926–2929, 2537; "Synthesis of D-Riboflavin-2-C and its Metabolism by *Lactobacillus casei*", Haley et al and Boron-Nitrogen Systems ..., Brown et al.
WPIL Data Base Reference (Cites U.S. Pat. No. 4,673,742 as listed above).

Primary Examiner—Donald G. Daus
Assistant Examiner—Diana G. Rivers
Attorney, Agent, or Firm—Oblon, Fisher, Spivak, McClelland & Maier

[57] ABSTRACT

Riboflavin of the formula I

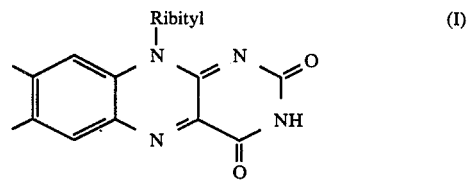

is prepared by an improved process by condensing a 4,5-dimethyl-N-(D)-ribityl-2-phenylazoaniline of the formula II

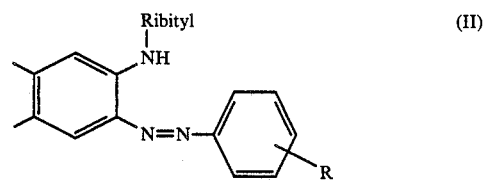

where R is H, —CL, —NO₂, —CH₃ or —OCH₃ in the o- or p-position, with barbituric acid of the formula III

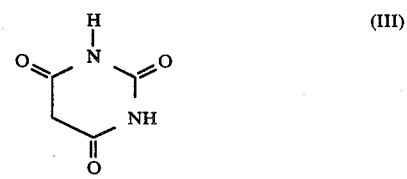

in the presence of an acid as a condensing agent, by a process in which the acidic condensing agent used is an aliphatic secondary carboxylic acid of the general formula IV

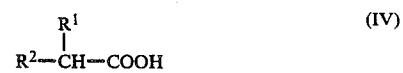

where $R^1$ is methyl or ethyl and $R^2$ is alkyl of 3 or 4 carbon atoms.

20 Claims, No Drawings

PREPARATION OF RIBOFLAVIN

The present invention relates to an improved process for the preparation of riboflavin (I; vitamin $B_2$) by condensation of a 4,5-dimethyl-N-(D)-ribityl-2-phenylazoaniline (II) with barbituric acid (III) in the presence of an acid as a condensing agent.

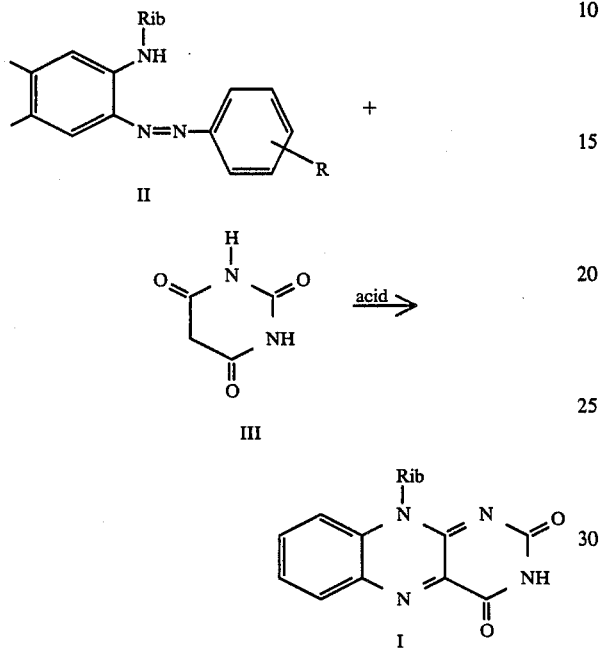

Rib=ribityl
R=H or p- or o-substituent, such as —Cl, —$NO_2$ or —$CH_3$.

Apart from the improvement according to the invention, this final step of the riboflavin synthesis has been disclosed in a number of publications, for example by Tishler et al. (J. Am. Chem. Soc. 69 (1947), 1487), where glacial acetic acid was used as the acidic condensing agent.

Berezowskii et al. (J. Gen. Chem. USSR 1961, page 3444) also investigated a number of other acids with regard to their suitability as condensing agents. According to this publication, the best yields of I, about 70%, were obtained using acetic acid, phenylacetic acid and benzoic acid. However, they used an excess of 65 mol% of barbituric acid. If, on the other hand, II and III are used in equimolar amounts, the yield of I decreases substantially. For example, Haley et al. (J. Am. Chem. Soc. 76 (1954), 2926) obtained riboflavin in a yield of only 41% using glacial acetic acid as the condensing agent in the reaction of II and III in a molar ratio of 1:1.

Much better results were obtained in the process of German Laid-Open Application DOS No. 3,302,497. In this process, aliphatic or cycloaliphatic-aliphatic tertiary carboxylic acids, in particular trimethylacetic acid (pivalic acid) and suitable commercial mixtures of synthetic acids which essentially contain saturated tertiary carboxylic acids were used as acidic condensing agents. Versatic ® 10-acid, a synthetic $C_{10}$-carboxylic acid from Shell Chemie, and similar products from Esso, which are commercially available under the name neoacids (eg. neodecanoic acid), were used as catalysts and are particularly advantageous.

Although this process can be carried out very advantageously even on an industrial scale, it is still unsatisfactory in some respects. On the one hand, the proposed acids, such as Versatic ® 10-acid, are not commercially available in unrestricted amounts and are very expensive.

Furthermore, recovery, by distillation, of the liquid tertiary carboxylic acids, such as Versatic ® 10-acid, which are particularly advantageous per se, is relatively expensive since their boiling range (90% of the mixture boils at 280° C. under atmospheric pressure) is relatively high, and a fairly large residue which cannot be processed remains when the acid mixture is worked up by distillation after the reaction.

It is an object of the present invention to provide an acidic catalyst which is industrially even more readily obtainable and therefore even cheaper, and which can readily be recovered by distillation.

We have found that this object is achieved and that, surprisingly, 2-ethylhexanoic acid, which is used in the preparation of plasticizers and is therefore prepared industrially on a large scale, and hence economically, and certain homologs of this acid, do not possess the disadvantages of the prior art which have been described.

The present invention accordingly relates to an improved process for the preparation of riboflavin of the formula I

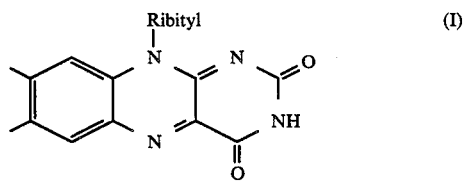

by condensing a 4,5-dimethyl-N-(D)-ribityl-2-phenylazoaniline of the formula II

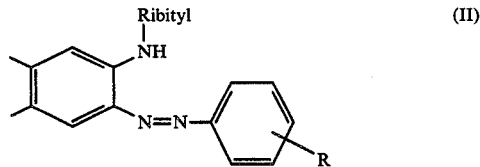

where R is H, —Cl, —$NO_2$, —$CH_3$ or —$OCH_3$ in the o- or p-position, with barbituric acid of the formula III

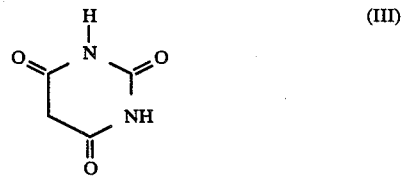

in the presence of an acid as a condensing agent, wherein the acidic condensing agent used is an aliphatic secondary carboxylic acid of the general formula IV

where $R^1$ is methyl or ethyl and $R^2$ is alkyl with 3 or 4 carbon atoms.

This is particularly surprising since lower secondary carboxylic acids, such as isobutyric acid, are far from suitable as catalysts. For example, Comparative Example 4 in German Laid-Open Application DOS No. 3,302,497 shows that isobutyric acid is disadvantageous as a catalyst acid.

Suitable aliphatic secondary carboxylic acids of the formula IV are α-methyl- and α-ethylhexanoic acid and α-methyl- and α-ethylheptanoic acid. Of particular importance is α-ethylhexanoic acid, which is readily available industrially. It has a boiling range of from 224° to 230° C. under 1,013 mbar, this boiling range thus being about 50° lower than that of Versatic ® 10-acid.

The starting compounds II and their preparation are known. In general, the cheapest compound of this series, ie. the phenylazo derivative, is used. However, compounds in which the ortho position or, in particular, the para position of the azophenyl group is substituted by substituents such as methyl, chlorine, methoxy or nitro are in principle also suitable. The starting compounds need not be specially purified but may also be employed in the form of crude products. In this case, the yields are based on II present in the starting material.

As conventionally carried out in the past, the reaction is advantageously effected in the presence of an inert diluent or solvent.

Preferred solvents are those in which some or all of the water formed during the condensation is soluble, ie. dioxane, tetrahydrofuran, 1-methoxypropanol, dimethylformamide, N-methylpyrrolidone and especially the relatively cheap lower alcohols having a boiling point of from 80° to 150° C., such as propanol, isopropanol, n-butanol, isobutanol and n-pentanol, in particular isobutanol.

The amount of solvent should advantageously be such that the starting compounds can just be brought into solution. This amount is in general from 2 to 12 l per kg of II. After heating has been carried out for a short time, the riboflavin formed begins to crystallize out.

The amount of carboxylic acid is preferably from 0.5 to 6 moles per mole of II. The yields obtained in this process are about 80%, but can be increased further to above 90% if III is used in an excess of up to 0.15 mole. A larger excess has no adverse effect but does not result in any noticeable increase in yield.

The reaction temperatures are from 80° to 120° C. The reaction is preferably carried out at above 100° C., ie. about 100°–115° C., and in a solvent having an appropriately high boiling point, especially isobutanol. At 100° C., the reaction time is about 5–15 hours.

Where an alcohol, such as isobutanol, is employed as the solvent, the acids according to the invention have the advantage that they show hardly any tendency to esterification, so that there is virtually no loss of solvent and acid, or the corresponding regeneration can be dispensed with. It is also particularly simple to wash out the residual acid from the riboflavin.

The reaction mixture can be worked up by a conventional method, for example by allowing it to cool and filtering off the crystalline riboflavin.

EXAMPLE 1 AND COMPARATIVE EXAMPLES 1a AND 1b

A. In each case, a mixture consisting of 40 g of technical grade 4,5-dimethyl-N-(D)-ribitylphenylazoaniline (containing 85–88% by weight of the 2-phenylazo derivative II which can be cyclized to riboflavin (I), corresponding to 0.096 mole) and 16 g (0.124 mole) of barbituric acid, the amount of isobutanol shown in Table 1 and the acid stated in Table 1 was heated at the boil (108°–110° C.) for 10 hours, while stirring and cooling. Thereafter, the reaction mixtures were cooled to 60° C., and the crude I which had crystallized out was filtered off under suction, washed with 200 ml of hot water at 80° C. and 200 ml of methanol and then dried. Table 1 shows the amount of crude I formed, the associated theoretical yield of crude I, based on 4,5-dimethyl-N-(D)-ribityl-2-phenylazoaniline present, and the amount of crude 1 obtained per kg of starting compound used.

B. 20 g of the crude I prepared as described in A, in each case, were suspended in 200 ml of water, the suspension was heated to 40° C., 10 g of a 25% strength by weight aqueous NaOH were added and the reaction mixture was then stirred for 15 minutes. Thereafter, the resulting solution was pumped in the course of 15 minutes into a mixture of 200 ml of water and 15 g of concentrated HCl at from 98° to 100° C., and the resulting reaction solution was stirred for a further hour at this temperature and then cooled to 40° C. The resulting crystals of pure I were then washed with 200 ml of hot water at 60° C. and 200 ml of methanol. Table 1 shows the amount of pure I obtained, the yield of pure I based on crude I used, and the theoretical yields of pure I, based on 4,5-dimethyl-N-(D)-ribityl-2-phenylazoaniline present in the starting compound.

The experiments show that 2-ethylhexanoic acid is much more suitable as an acidic catalyst for the preparation of I than the acetic acid conventionally used to date industrially, and is at least as good as the Versatic ® 10-acid which is preferably used in the process of German Laid-Open Application DOS No. 3,302,497, and compared with which the acid according to the invention is superior in terms of its availability and technical handling.

TABLE 1

| Example | Comparative example | II [mole] | Isobutanol [ml] | Acid [ml] | Yields of crude riboflavin | | | Yields of pure riboflavin | | |
|---|---|---|---|---|---|---|---|---|---|---|
| | | | | | Amount [g] | [% based on pure II] | [kg, based on mg of II used] | Amount [g] | [%, based on crude I] | [% of theory, based on pure II] |
| 1 | | technical grade 0.096 | 200 | ethyl-hexanoic acid 60 | 34.6 | 95.7 | 0.865 | 17.9 | 89.5 | 85.7 |
| | 1a | technical grade 0.096 | 170 | Versatic 10-acid 100 | 33.0 | 93.8 | 0.848 | 18.2 | 91 | 85.4 |
| | 1b | technical grade | 200 | glacial acetic | 33.0 | 91.32 | 0.825 | 17.9 | 89.5 | 81.7 |

TABLE 1-continued

| Example | Comparative example | II [mole] | Isobutanol [ml] | Acid [ml] | Yields of crude riboflavin Amount [g] | [% based on pure II] | [kg, based on mg of II used] | Yields of pure riboflavin Amount [g] | [%, based on crude I] | [% of theory, based on pure II] |
|---|---|---|---|---|---|---|---|---|---|---|
| | | 0.096 | | acid 20 | | | | | | |

EXAMPLES 2 TO 6

In each case, a mixture consisting of 40 g of technical grade (89–91% strength by weight) 4,5-dimethyl-N-(D)-ribitylphenylazoaniline (containing the molar amount shown in Table 2 of the 2-phenylazo derivative II which can be cyclized to I) and 16 g (0.124 mole) of barbituric acid, the amount of isobutanol shown in Table 2 and the amount of 2-ethylhexanoic acid shown in the same table was reacted, the reaction mixture worked up and the product purified, these steps being carried out similarly to Example 1.

The results obtained are shown in Table 2, in a manner similar to that in which the results of Example 1 are represented in Table 1.

from 90 to 91% by weight of the 2-phenylazo derivative II which can be cyclized to I; corresponding to 0.05 mole) and 8 g of barbituric acid, 40 ml of 2-methylvaleric acid and 100 ml of isobutanol was refluxed for 10 hours while stirring. Thereafter, the reaction mixture was cooled to 60° C., and the crude I which had crystallized out was filtered off under suction, washed with 100 ml of methanol and 100 ml of hot water at 60° C. and then dried.

The yield was 17.5 g of crude I, corresponding to 93% of theory, based on pure II.

15 g of crude I was subjected to a purification procedure similar to that described in I, to obtain a very pure product. 12.7 g of pure I were obtained, corresponding to 78.74% of theory, based on pure II.

TABLE 2

| Example | II [mole] | Isobutanol [ml] | Ethylhexanoic acid [ml] | Yields of crude riboflavin Amount [g] | [%, based on pure II] | [kg per kg of II used] | Yields of pure riboflavin Amount [g] | [%, based on crude I] | [% of theory, based on pure II] |
|---|---|---|---|---|---|---|---|---|---|
| 2 | 0.1 mole | 170 | 100 | 35.4 | 94.2 | 0.885 | 18.1 | 90.1 | 85.2 |
| 3 | 0.1 mole | 200 | 60 | 35.2 | 93.6 | 0.880 | 18.0 | 90 | 84.3 |
| 4 | 0.1 mole | 200 | 60 | 35.3 | 93.6 | 0.883 | 18.0 | 90 | 84.5 |
| 5 | 0.1 mole | 160 | 80 | 34.9 | 92.8 | 0.873 | 18.1 | 90.5 | 84.0 |
| 6 | 0.1 mole | 180 | 40 | 35.0 | 93.1 | 0.875 | 18.2 | 91 | 84.7 |

EXAMPLES 7 TO 10

In each case, a mixture consisting of 40 g of technical grade 4,5-dimethyl-N-(D)-ribitylphenylazoaniline (containing from 90 to 91% of the 2-phenylazo derivative II which can be cyclized to I; corresponding to 0.1 mole) and 16 g (0.124 mole) of barbituric acid, 80 ml of 2-ethylhexanoic acid and the solvent stated in Table 3 in the amount shown there were stirred under reflux for 10 hours. After cooling to room temperature, the mixture was filtered under suction and the I separated off was washed with methanol and with hot water at 80° C. and then dried. The crude I obtained in this manner was then purified similarly to Example 1B. Table 3 shows the resulting amounts and theoretical yields (based on the pure 2-phenylazo isomer (II) present in the technical grade 4,5-dimethyl-N-(D)-ribitylphenylazoaniline) of the crude I and pure I obtained in each case.

I claim:

1. An improved process for the preparation of riboflavin of the formula I

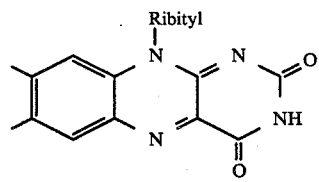

by condensing a 4,5-dimethyl-N-(D)-ribityl-2-phenylazoaniline of the formula II

TABLE 3

| Example | Solvent [ml] | Yield of crude I Amount [g] | [%, based on pure II] | [kg per kg of II used] | Yield of pure I Amount [g] | [%, based on crude I] | [%, based on pure II] |
|---|---|---|---|---|---|---|---|
| 7 | Dioxane 180 | 35.3 | 93.8 | 0.88 | 18.4 | 92 | 86.3 |
| 8 | 2-Butanol 200 | 34.5 | 91.66 | 0.86 | 18.4 | 92 | 84.3 |
| 9 | Methoxypropanol 200 | 35.7 | 94.85 | 0.89 | 18.2 | 91 | 86.3 |
| 10 | Pentanol 200 | 35.2 | 93.5 | 0.88 | 18.0 | 90 | 84.2 |

EXAMPLE 11

A mixture consisting of 20 g of technical grade 4,5-dimethyl-N-(D)-ribitylphenylazoaniline (containing

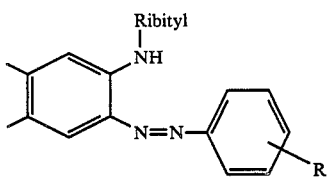
(II)

where R is H, —Cl, —NO₂, —CH₃ or —OCH₃ in the o- or p-position, with barbituric acid of the formula III

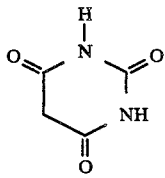
(III)

in the presence of an acid as a condensing agent, wherein the acidic condensing agent used is an aliphatic secondary carboxylic acid of the formula IV

(IV)

where $R^1$ is methyl or ethyl and $R^2$ is alkyl of 3 or 4 carbon atoms.

2. A process for the preparation of riboflavin of formula (I)

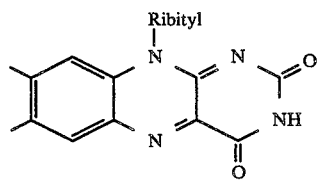

said process comprising:
condensing a 4,5-dimethyl-N-(D)-ribityl-2-phenylazoaniline of formula (II)

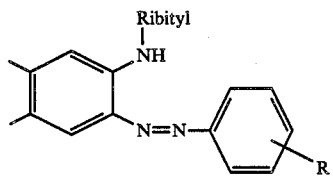

wherein R is hydrogen, chlorine, nitro, methyl or methoxy and R is situated at the ortho- or paraposition, with barbituric acid of formula (III)

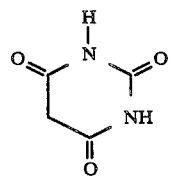

in the presence of an acid condensing agent of formula (IV)

$(R^1)(R^2)CH—COOH$ wherein $R^1$ is methyl or ethyl, and $R^2$ is a $C_{3-4}$ alkyl group or a linear $C_5$ alkyl group.

3. The process of claim 1, wherein said acid condensing agent of formula (IV) comprises 2-ethylhexanoic acid.

4. The process of claim 2, wherein said acid condensing agent of formula (IV) comprises α-methylhexanoic acid, α-ethylhexanoic acid, α-methylheptanoic acid, or α-ethylheptanoic.

5. The process of claim 1, wherein said 4,5-dimethyl-N-(D)-ribityl-2-phenylazoaniline of formula (II) is substituted at the para-position by methyl, chlorine, methoxy or nitro.

6. The process of claim 2, wherein said 4,5-dimethyl-N-(D)-ribityl-2-phenylazoaniline of formula (II) is substituted at the para-position by methyl, chlorine, methoxy or nitro.

7. The process of claim 1, wherein said 4,5-dimethyl-N-(D)-ribityl-2-phenylazoaniline of formula (II) is substituted at the ortho-position by methyl, chlorine, methoxy, or nitro.

8. The process of claim 2, wherein said 4,5-dimethyl-N-(D)-ribityl-2-phenylazoaniline of formula (II) is substituted at the ortho-position by methyl, chlorine, methoxy, or nitro.

9. The process of claim 1, comprising using a diluent or solvent.

10. The process of claim 2, comprising using a diluent or solvent.

11. The process of claim 9, comprising using, as said diluent or solvent, dioxane, tetrahydrofuran, 1-methoxypropanol, dimethylformamide, n-methylpyrrolidone or a lower alcohol having a boiling point of from 80° to 150° C.

12. The process of claim 10, comprising using, as said diluent or solvent, dioxane, tetrahydrofuran, 1-methoxypropanol, dimethylformamide, N-methylpyrrolidone, or a lower alcohol having a boiling point of from 80° to 150° C.

13. The process of claim 11, wherein said lower alcohol having a boiling point of from 80° to 150° C. is propanol, isopropanol, n-butanol, isobutanol or n-pentanol.

14. The process of claim 12, wherein said lower alcohol having a boiling of from 80° to 150° C. is propanol, isopropanol, n-butanol, isobutanol or n-pentanol.

15. The process of claim 11, comprising using said diluent or solvent, in an amount of from 2 to 12 liter per kg of said 4,5-dimethyl-N-(D)-ribityl-2-phenylazoaniline of formula (II).

16. The process of claim 12, comprising using said diluent or solvent, in an amount of from 2 to 12 liter of diluent or solvent per kg of said 4,5-dimethyl-N-(D)-ribityl-2-phenylazoaniline of formula (II).

17. The process of claim 1, comprising using said acid condensing of formula (IV) in an amount of from 0.5 to 6 mol per mol of said 4,5-dimethyl-N-(D)-ribityl-2-phenylazoaniline (II).

18. The process of claim 2, comprising using said acid condensing agent of formula (IV) in an amount of from 0.5 to 6 mol per mol of said 4,5-dimethyl-N-(D)-ribityl-2-phenylazoaniline of formula (II).

19. The process of claim 1, comprising using a reaction temperature of from 80° to 120° C.

20. The process of claim 2, comprising using a reaction temperature of from 80° to 120° C.

* * * * *